(12) United States Patent
Zhang et al.

(10) Patent No.: US 10,627,419 B2
(45) Date of Patent: Apr. 21, 2020

(54) NANOROBOT

(71) Applicant: BOE TECHNOLOGY GROUP CO., LTD., Beijing (CN)

(72) Inventors: Yifei Zhang, Beijing (CN); Zuo Yuan, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 321 days.

(21) Appl. No.: 15/539,332

(22) PCT Filed: Oct. 24, 2016

(86) PCT No.: PCT/CN2016/103006
§ 371 (c)(1),
(2) Date: Jun. 23, 2017

(87) PCT Pub. No.: WO2017/173811
PCT Pub. Date: Oct. 12, 2017

(65) Prior Publication Data
US 2018/0074083 A1 Mar. 15, 2018

(30) Foreign Application Priority Data
Apr. 6, 2016 (CN) .......................... 2016 1 0211041

(51) Int. Cl.
*G01N 35/00* (2006.01)
*B01L 3/00* (2006.01)
(Continued)

(52) U.S. Cl.
CPC ............ *G01N 35/0099* (2013.01); *B01L 3/52* (2013.01); *G01N 33/58* (2013.01);
(Continued)

(58) Field of Classification Search
CPC .............. G01N 35/0099; G01N 33/58; G01N 35/1002; B01L 3/52; B01L 2300/0896; B01L 2200/16
See application file for complete search history.

(56) References Cited

U.S. PATENT DOCUMENTS 7,785,774 B2   8/2010   Yue
2011/0008446 A1   1/2011   Yu et al.

FOREIGN PATENT DOCUMENTS

CN   1789425 A   6/2006
CN   101085389 A   12/2007
(Continued)

OTHER PUBLICATIONS

Translation of Jiang Huaiwei et al; Research and Progress in Bio-Nano-Robots, 2005, Robot, vol. 27(6)569-574 (Year: 2005).*
(Continued)

*Primary Examiner* — Bradley J Osinski
(74) *Attorney, Agent, or Firm* — Collard & Roe, P.C.

(57) ABSTRACT

A nanorobot, comprising: a load part, configured to load a labeling reagent; a power part, configured to generate power according to an environmental condition, a direction of the power being a direction away from the load part; and a connecting part, respectively connected with the load part and the power part, so that the power part seals the load part, wherein, the connecting part is configured to be disconnected when the power is greater than a preset value.

11 Claims, 3 Drawing Sheets

(51) Int. Cl.
*G01N 33/58* (2006.01)
*G01N 35/10* (2006.01)

(52) U.S. Cl.
CPC ...... *G01N 35/1002* (2013.01); *B01L 2200/16* (2013.01); *B01L 2300/046* (2013.01); *B01L 2300/0896* (2013.01); *G01N 2035/1034* (2013.01); *G01N 2333/475* (2013.01)

(56) References Cited

FOREIGN PATENT DOCUMENTS

| | | |
|---|---|---|
| CN | 101744645 A | 6/2010 |
| CN | 102481259 A | 5/2012 |
| CN | 104020298 A | 9/2014 |
| CN | 105695327 A | 6/2016 |
| CN | 205501323 A | 8/2016 |
| JP | 2016-014074 A | 1/2016 |

OTHER PUBLICATIONS

Liu, Handan et al. "Bio-nano-robot and Drug Targeting Delivery Technology", Chinese Journal of Mechanical Engineering, vol. 44, No. 11, Nov. 2008, pp. 80-86.
Liu, Ying. "Research on Energy Storage Model of Atphase Molecular Motor", Southwest Jiaotong University Master Degree Thesis, May 20, 2013.
Chinese Office Action in Chinese Application No. 201610211041.4, dated Aug. 3, 2017 with English translation.
International Search Report of PCT/CN2016/103006 in Chinese, dated Jan. 25, 2017 with English translation.
Notice of Transmittal of the International Search Report of PCT/CN2016/103006 in Chinese, dated Jan. 25, 2017.
Written Opinion of the International Searching Authority of PCT/CN2016/103006 in Chinese, dated Jan. 25, 2017 with English translation.
Jiang, Huai-wei et al. "Research and Progress in Bio-nano-robot", Robot, vol. 27, No. 6, Nov. 2005, pp. 569-574.

* cited by examiner

US 10,627,419 B2

NANOROBOT

CROSS REFERENCE TO RELATED APPLICATIONS

This application is the National Stage of PCT/CN2016/103006 filed on Oct. 24, 2016, which claims priority under 35 U.S.C. § 119 of Chinese Application No. 201610211041.4 filed on Apr. 6, 2016, the disclosure of which is incorporated by reference.

TECHNICAL FIELD

Embodiments of the present disclosure relate to a nanorobot applied to a medical technology field.

BACKGROUND

An existing anti-cancer drug mostly enters a human body through oral administration, infusion, etc., which, when inhibiting and killing cancer cells, also affects normal cells in the human body as well, and seriously affects health of a patient. Anti-cancer drugs, for example, bleomycin, mitomycin, etc. are currently widely used anti-cancer drugs, which, however, have obvious side effects, and are apt to cause a variety of symptoms such as anemia and vomiting; therefore, their direct use is neither conducive to the health of the patient, nor conducive to diagnosis and treatment of cancer.

In order to effectively treat cancer, the cancer cells are labeled with tumor specific markers such as alpha-fetoprotein (AFP), carcinoembryonic antigen (CEA), and neuron-specific enolase (NSE) in the prior art; however, the above-described markers all lack versatility, they can only reflect a few types or one type of malignant tumor, with no diagnostic value with respect to other malignant tumors, and their labeling process is not controllable, so it is difficult to perform targeted labeling according to a user's need.

SUMMARY

A nanorobot is provided in the embodiments of this disclosure, comprising: a load part, configured to load a labeling reagent; a power part, configured to generate power according to an environmental condition, a direction of the power being a direction away from the load part; and a connecting part, respectively connected with the load part and the power part, so that the power part seals the load part, wherein, the connecting part is configured to be disconnected when the power is greater than a preset value.

BRIEF DESCRIPTION OF THE DRAWINGS

In order to make the embodiments of the disclosure apparent, the drawings related to the embodiments of the disclosure will be described briefly. Apparently, the described embodiments are just a part of the embodiments of the disclosure. For those skilled in the art, he or she can obtain other figure(s) according to these figures, without any inventive work.

DETAILED DESCRIPTION

The technical solutions of the embodiments will be described in a clearly and fully understandable way in connection with the drawings related to the embodiments of the invention. Apparently, the described embodiments are just a part but not all of the embodiments of the invention. Based on the described embodiments herein, those skilled in the art can obtain other embodiment(s), without any inventive work, which should be within the scope of the invention.

Figure 1:
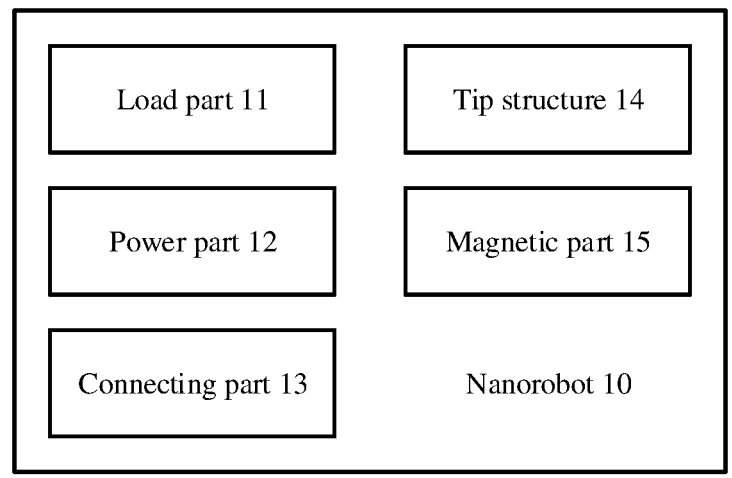
FIG. 1 shows a schematic block diagram of a nanorobot according to an embodiment of the present disclosure.
Figure 2:
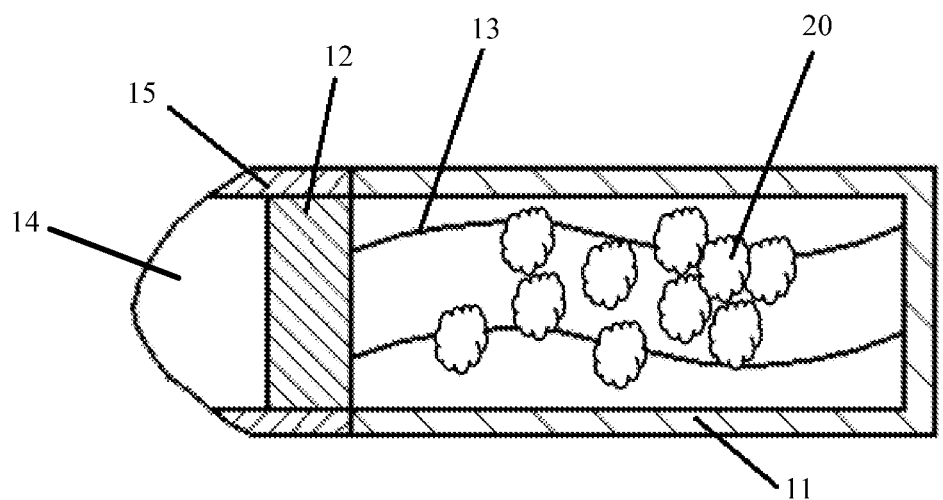
FIG. 2 shows a structural schematic diagram of the nanorobot according to the embodiment of the present disclosure.

As shown in FIG. 1 and FIG. 2, a nanorobot 10 according to an embodiment of the present disclosure, comprises:

A load part 11, configured to load a labeling reagent 20;

A power part 12, configured to generate power according to an environmental condition, a direction of the power being a direction away from the load part 11;

A connecting part 13, with both ends being respectively connected with the load part 11 and the power part 12, so that the power part 12 seals the load part 11, and which is disconnected when the power is greater than a preset value.

Figure 3:
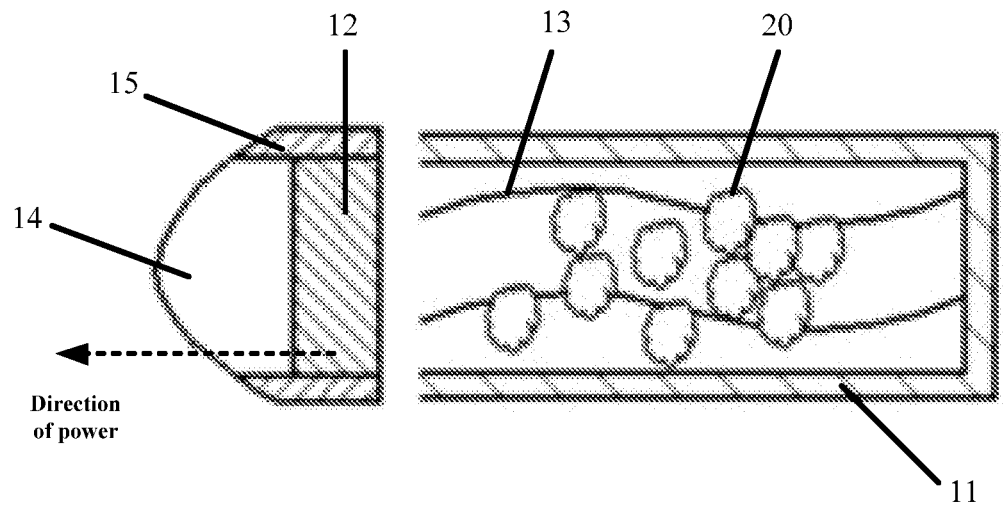
FIG. 3 and FIG. 4 show a schematic diagram of the nanorobot releasing a labeling reagent according to the embodiment of the present disclosure.
Figure 4:
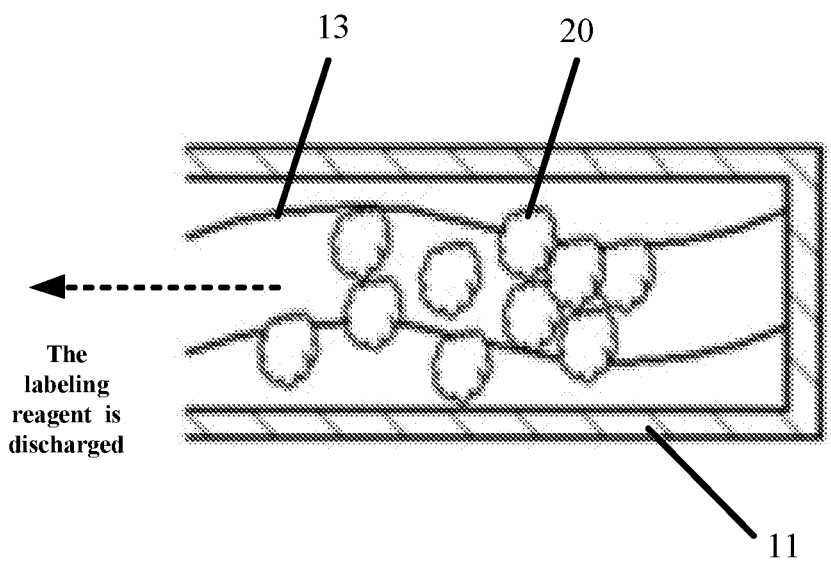

According to this embodiment, since the power part 12 can generate power according to the environmental condition, the user can set the environmental condition according to needs (for example, when it is estimated that the nanorobots reach an infected part or scatter all around a patient's body), so that the power generated by the power part 12 is greater than the preset value, and further, the connecting part 13 is disconnected, the power part 12 is disengaged from the load part 11 (as shown in FIG. 3), and the labeling reagent 20 in the load part 11 is discharged (as shown in FIG. 4). Thus, labeling diseased cells according to needs is implemented, so that a doctor can accurately determine distribution of the diseased cells in the patient's body, and further accurately determine distribution of the diseased cells in the patient's body, so as to determine a state of illness and treat the disease.

For example, as shown in FIG. 2, one end of the connecting part 13 is connected with an inner wall of the load part 11, and the other end thereof is connected with a side of the power part 12 close to the load part 11.

According to this embodiment, the connecting part 13 is located inside the load part 11, which is conducive to reduction of a volume of the nanorobot 10, and is conducive to injection.

For example, as shown in FIG. 2, the nanorobot 10 further comprises:

A tip structure 14, provided on a side of the power part 12 away from the load part 11.

According to this embodiment, a certain amount of blood can be extracted from the patient's body, and then the nanorobot is injected into an erythrocyte of the blood (e.g., by means of cell microinjection), and then the erythrocyte is injected into the patient's body (e.g., by means of intravenous injection).

When the power part 12 generates power, it can drive the nanorobot to move in a direction of the power. Through the tip structure 14, it is convenient for the nanorobot to puncture an erythrocyte wall, so as to label the diseased cells outside the erythrocyte.

For example, as shown in FIG. 2, the nanorobot 10 further comprises:

A magnetic part 15, configured to drive the nanorobot 10 to move according to an induced magnetic force.

According to this embodiment, the nanorobot may be guided to move by setting an external magnetic field (when the nanorobot is located in the erythrocyte, movement of the nanorobot can drive the erythrocyte to move together; as long as it is ensured that the power generated by the power part is relatively small, the tip structure 14 will not puncture the erythrocyte wall), in order to guide the nanorobot to a site which needs to be labeled, and then release the labeling reagent, to provide a user with a greater operating space.

For example, as shown in FIG. 2, the magnetic part 15 is provided on the power part 12, wherein, when the magnetic part 15 is located in a predetermined magnetic field, a direction of the magnetic force borne is same as the direction of the power. When the magnetic part 15 is located in the predetermined magnetic field, the direction of the magnetic force borne is same as the direction of the power generated by the power part, so that the power part 12 can be pulled in the direction away from the load part 11, and further a certain auxiliary force may be provided for separating the power part 12 from the load part 11, so as to release the labeling reagent as soon as possible.

Figure 5:
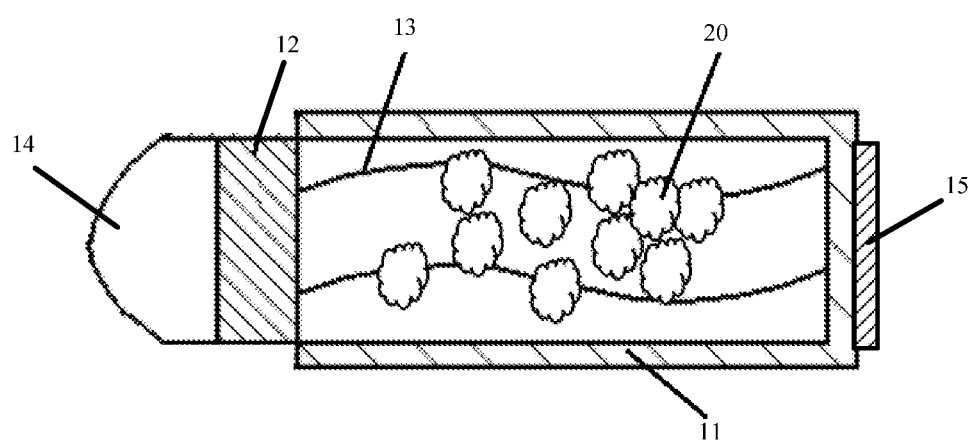
FIG. 5 shows a structural schematic diagram of a nanorobot according to a further embodiment of the present disclosure.

For another example, as shown in FIG. 5, the magnetic part 15 may also be provided on a side of the load part 11 away from the power part 12, wherein, when the magnetic part 15 is located in a predetermined magnetic field, a direction of the magnetic force borne is opposite to the direction of the power. When the magnetic part 15 is located in the predetermined magnetic field, the direction of the magnetic force borne is opposite to the power generated by the power part 12, so that the load part 11 can be pulled in a direction away from the power part 12, and further a certain auxiliary force may be provided for separation of the power part 12 from the load part 11, so as to release the labeling reagent as soon as possible.

For example, as shown in FIG. 2, a length of the load part 11 parallel to the direction of the power is greater than a length perpendicular to the direction of the power. According to this embodiment, it is possible that nanorobot is subjected to a smaller resisting force when moving along the direction of the power. For example, the load part 11 may be of a cylindrical shape or a prismatic shape.

For example, the power part 12 is an adenosine triphosphate molecular motor.

The adenosine triphosphate molecular motor is just the ATP molecular motor, the molecular motor may be a motor with $F_1$ATPase as a core, and with an F0 complex as an engine part, whose energy is supplied by the ATP, which is characterized by a fact that it is reversible by ATP hydrolysis/synthesis, and thus is more efficient. Moreover, the molecular motor can be started up or turned off as well as change power according to influence of an environmental magnetic field, which is convenient to control. For example, when the environmental magnetic field increases to a certain value, the ATP molecular motor is started up, driving the nanorobot to move along the direction of the power; and when the environmental magnetic field is further increased, the power generated by the ATP molecular motor increases, so that the ATP molecular motor is disengaged from the connecting part.

For example, the connecting part 13 is an inorganic nanometer material. The inorganic nanometer material is generally harmless to the human body, and can be excreted out of the body with human waste. Of course, the load part 11 may also be provided as an organic nanometer material according to needs.

For example, the labeling reagent is configured to label a tumor specific growth factor.

The tumor specific growth factor (TSGF) is a result of extensive amplification of a malignant tumor and peripheral capillaries, and is gradually released to peripheral blood with formation and growth of the tumor; generally, in a region with higher TSGF concentration, a tumor symptom is more severe. Therefore, a cancer affected part, as well as severity of respective affected parts, may be determined by labeling the TSGF.

For example, the nanorobot 10 has a volume of 4 to 16 cubic micrometers.

Since a volume of a human erythrocyte is generally between 40 and 160 cubic micrometers, the volume of the nanorobot is set to be 1/10 of the volume of the erythrocyte, which is conducive to its injection into the erythrocyte by means of cell microinjection.

The technical solutions of the present disclosure are described above in details in connection with the drawings. In a related art, a labeling process of the diseased cells is uncontrollable, and it is difficult to perform targeted labeling according to the user's needs. According to the technical solution of the embodiment of the present disclosure, since the power part can generate power according to the environmental condition, the user can set the environmental condition according to needs, so that the power generated by the power part is greater than the preset value when necessary, and further, the connecting part is disconnected, the power part is disengaged from the load part, and the labeling reagent in the load part is discharged, so as to label the diseased cells. Thus, the doctor can accurately determine the distribution of the diseased cells in the patient's body, so as to determine the state of illness and treat the disease.

In this disclosure, the relationship terms such as "first" and "second" are only used to depart an object or an operation from another object or an operation, but not always intended to require or imply that any actual relationship or sequence exist in these objects or operation. Furthermore, the terms "include", "including" etc. are intended to cover non-exclusive including, therefore the process, method, article or device including a series of elements not only includes those elements, but also includes other elements which are not listed out, or also includes inherent elements of this process, method, article or device. Without other limitation, the elements limited with "includes one", does not exclude the condition that other same elements exist in the process, method, article or device including said elements.

Obviously, the skilled in the art may make all kinds of changes and modification without breaking out from the spirit and the scope of this disclosure. Thus, if these changes and modification of this disclosure are fallen into the scope of claims of this disclosure and equal technology thereof, then the disclosure also intends to include these changes and modification.

What are described above is related to the illustrative embodiments of the disclosure only and not limitative to the scope of the disclosure. Obvious variations and replacement by any one of the skilled person in the art in the technical scope of the disclosure should be all covered in the scope of this disclosure. The scopes of the disclosure are defined by the accompanying claims.

The present application claims the priority of the Chinese Patent Application No. 201610211041.4 filed on Apr. 6, 2016, which is incorporated herein in its entirety by reference as part of the disclosure of the present application.

The invention claimed is:

1. A nanorobot, comprising:
   a load part, configured to load a labeling reagent;
   a power part, configured to generate power according to an environmental condition, a direction of the power being a direction away from the load part; and
   a connecting part, respectively connected with the load part and the power part, so that the power part seals the load part, wherein, the connecting part is configured to be disconnected when the power is greater than a preset value.

2. The nanorobot according to claim 1, wherein, one end of the connecting part is connected with an inner wall of the load part, and the other end thereof is connected with a side of the power part close to the load part.

3. The nanorobot according to claim 2, further comprising:
   a tip structure, provided on a side of the power part away from the load part.

4. The nanorobot according to claim 3, further comprising:
   a magnetic part, configured to drive the nanorobot to move according to an induced magnetic force.

5. The nanorobot according to claim 4, wherein,
   the magnetic part is provided on the power part; and
   when the magnetic part is located in a predetermined magnetic field, a direction of the magnetic force borne is same as the direction of the power.

6. The nanorobot according to claim 4, wherein,
   the magnetic part is provided on a side of the load part away from the power part; and
   when the magnetic part is located in a predetermined magnetic field, a direction of the magnetic force borne is opposite to the direction of the power.

7. The nanorobot according to claim 2, wherein, a length of the load part parallel to the direction of the power is greater than a length of the load part perpendicular to the direction of the power.

8. The nanorobot according to claim 1, wherein, the power part is an adenosine triphosphate molecular motor.

9. The nanorobot according to claim 1, wherein, the connecting part is an inorganic nanometer material.

10. The nanorobot according to claim 1, wherein, the labeling reagent is configured to label a tumor specific growth factor.

11. The nanorobot according to claim 1, wherein, the nanorobot has a volume of 4 to 16 cubic micrometers.

* * * * *